United States Patent
Goldfine et al.

(10) Patent No.: US 7,183,764 B2
(45) Date of Patent: Feb. 27, 2007

(54) METHOD FOR INSPECTING A CHANNEL USING A FLEXIBLE SENSOR

(75) Inventors: Neil J. Goldfine, Newton, MA (US); Darrell E. Schlicker, Watertown, MA (US); Vladimir Tsukernik, West Roxbury, MA (US); Ian C. Shay, Cambridge, MA (US); David C. Grundy, Reading, MA (US); Andrew P. Washabaugh, Chula Vista, CA (US)

(73) Assignee: JENTEK Sensors, Inc., Waltham, MA (US)

( * ) Notice: Subject to any disclaimer, the term of this patent is extended or adjusted under 35 U.S.C. 154(b) by 124 days.

(21) Appl. No.: 10/650,486

(22) Filed: Aug. 28, 2003

(65) Prior Publication Data

US 2004/0124834 A1    Jul. 1, 2004

Related U.S. Application Data

(63) Continuation-in-part of application No. 10/348,339, filed on Jan. 21, 2003, now Pat. No. 6,798,198, which is a continuation of application No. 10/172,834, filed on Jun. 13, 2002, now abandoned, and a continuation-in-part of application No. 10/102,606, filed on Mar. 19, 2002, now abandoned, which is a continuation of application No. 09/946,146, filed on Sep. 4, 2001, now abandoned.

(60) Provisional application No. 60/407,436, filed on Aug. 29, 2002, provisional application No. 60/297,841, filed on Jun. 13, 2001, provisional application No. 60/231,776, filed on Sep. 12, 2000.

(51) Int. Cl.
   *G01N 27/82*    (2006.01)
   *G01N 27/72*    (2006.01)

(52) U.S. Cl. .................................... 324/238; 324/219

(58) Field of Classification Search ............... 324/219, 324/220, 221, 327, 238, 240, 242, 243, 261, 324/262
See application file for complete search history.

(56) References Cited

U.S. PATENT DOCUMENTS

| | | | |
|---|---|---|---|
| 2,622,125 A | 12/1952 | Bender | |
| 4,303,884 A | 12/1981 | Malick | |
| 4,668,912 A * | 5/1987 | Junker | ......................... 324/220 |
| 5,023,549 A | 6/1991 | Dau et al. | |
| 5,047,719 A | 9/1991 | Johnson et al. | |
| 5,278,498 A | 1/1994 | Vernon et al. | |
| 5,315,234 A | 5/1994 | Sutton, Jr. et al. | |
| 5,442,286 A | 8/1995 | Sutton, Jr. et al. | |
| 5,453,689 A | 9/1995 | Goldfine et al. | |
| 6,429,650 B1 * | 8/2002 | Kwun et al. | ................. 324/240 |

(Continued)

Primary Examiner—Jay M. Patidar
(74) Attorney, Agent, or Firm—Hamilton, Brook, Smith & Reynolds, P.C.

(57) ABSTRACT

Described are methods for pressurizing elastic support structures or balloons in sensor probes used for the inspection of components having areas of limited access. When inflated, the balloons press flexible sensors against the surface of the material under test. When deflated, the balloons permit easier insertion of the probes into the component and reduce the mechanical stresses on the sensors, thereby extending the sensor lifetime. By sequentially partially inserting the sensor into a limited access area from either side of the limited access area and scanning in opposite directions, the entire surface of the test material can be inspected.

14 Claims, 8 Drawing Sheets

U.S. PATENT DOCUMENTS 6,545,469 B1    4/2003  Batzinger et al.
6,715,370 B2 *  4/2004  Tasca ........................ 73/865.8
2002/0163333 A1 11/2002 Schlicker et al.
2003/0071615 A1 4/2003  Schlicker et al.
2003/0155914 A1 8/2003  Tsukernik et al.

* cited by examiner

METHOD FOR INSPECTING A CHANNEL USING A FLEXIBLE SENSOR

RELATED APPLICATIONS

This application is a continuation-in-part of U.S. application Ser. No. 10/348,339, filed Jan. 21, 2003, now U.S. Pat. No. 6,798,198 which is a continuation of U.S. application Ser. No. 10/172,834, filed Jun. 13, 2002, now abandoned which claims the benefit of U.S. Provisional Application No. 60/297,841, filed Jun. 13, 2001, and is a continuation-in-part of U.S. application Ser. No. 10/102,606, filed Mar. 19, 2002, now abandoned which is a continuation of U.S. application Ser. No. 09/946,146, filed Sep. 4, 2001, now abandoned which claims the benefit of U.S. Provisional Application No. 60/231,776, filed on Sep. 12, 2000, and claims the benefit of U.S. Provisional Application No. 60/407,436, filed Aug. 29, 2002. The entire teachings of the above applications are incorporated herein by reference.

BACKGROUND OF THE INVENTION

The nondestructive evaluation of materials for damage and defects often involves inspection of curved surfaces having limited access, such as engine disk slots, helicopter propulsion components, turbine blades, bolt holes, automotive components and other components with enclosed or partially enclosed regions having narrow openings. Typically, the defect is found when the inspection sensor, such as an eddy-current sensor, is brought into intimate contact with the surface. For coverage over wide areas of the surface, this inspection requires the use of sensors that are formed into the shape of the curved surface or are fabricated onto a flexible backing that can conform to the shape of the surface.

Compliant substrates, such as foam or ferrite loaded substrates, have been used to enhance the performance of eddy-current sensors and allow sensor arrays to conform to a surface through the compliance of the substrate. This is described, for example, by Goldfine (U.S. Pat. No. 5,453,689), Vernon (U.S. Pat. No. 5,278,498), Hedengren (U.S. Pat. No. 5,315,234) and Johnson (U.S. Pat. No. 5,047,719). While these non-rigid substrates offer the advantage of conforming to a wide range of complex shapes, they often require a rigid inner core to maintain the general shape. This can result in local variations in pressure on the sensor and a lack of adherence of the array to the surface of the material under test.

The shape of devices and gaps between devices has been controlled by the use of fluids such as water, air and oil for devices such as automobile tires, balloons used in angioplasty to clear arteries in the heart, and in air bearings. Often the desire is to maintain a specific shape without significant compliance after the shape has been established.

SUMMARY OF THE INVENTION

The disclosed invention addresses the limitations of using compressible solid substrates for inspection of confined material surfaces. Probe assembly structures and methods for using these assemblies which provide improved inspection capabilities and extend the useful life of the sensor are described herein. The probe assemblies may use fluid filled substrates enclosed in relatively rigid pre-shaped membrane materials or combinations of fluid filled "balloons" with compliant solids, such as foam or elastomers. Sensors placed on the surface of the shuttle may be used to inspect the material for flaws and defects or to characterize the material properties, such as coating thickness, electrical conductivity, or magnetic permeability.

In one embodiment of the invention, the surface of an area having limited access or a channel, such as an engine disk slot, a bolt hole, or a gun barrel, is inspected by inserting a probe and flexible sensor into the channel and then translating the sensor over the material surface. The probe contains a pressurizable chamber or balloon that facilitates the insertion of the probe into the channel when deflated and holds the sensor proximate to the test material surface when inflated. The chamber is pressurized after the probe is inserted into the channel to reduce the mechanical stress on the sensor associated with the insertion into the channel. The probe may also contain a rigid support to help maintain the sensor position near the material surface. In one embodiment of the invention, the sensor is an eddy-current sensor and in another embodiment is an eddy-current sensor array.

To provide inspection coverage near the edges of the channel, in one embodiment of the invention, the sensor is inserted into one channel opening at a distance less than one-half of the channel length and then the sensor response is measured as the sensor is pushed or moved through a second channel opening. In another embodiment of the invention, another scan is performed by deflating the balloon, reinserting or pulling the sensor back into the channel, inflating the balloon, and measuring the sensor response as the sensor is withdrawn from the channel. These sequential scans may provide complete coverage of the material surface along the scan path. In a preferred embodiment of the invention, the insertion distance is approximately one-third of the channel length. In one embodiment of the invention, a position encoder may be used to measure the sensor location so that the sensor data may be registered with respect to the physical distance.

Multiple scans may be performed on a given channel to ensure complete coverage or to improve confidence in the inspection. In one embodiment of the invention, two scans are performed with some overlap of the responses over the region near the center of the channel. The scan results may be shown individually or combined into a composite response. In a preferred embodiment of the invention, the response is combined by averaging the responses in the areas where the scans overlap.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows. The disclosed invention addresses the limitations of using compressible solid substrates for inspection of confined material surfaces. Probe assembly structures and methods for using these assemblies are described which provide improved inspection capabilities and extending the useful life of the sensor. The probe assemblies use fluid substrates enclosed in relatively rigid pre-shaped membrane materials or combinations of fluid filled "balloons" with compliant solids, such as foam or elastomers. Sensors placed on the surface of the shuttle are then used to inspect the material for flaws and defects or to characterize the material properties, such as coating thickness, electrical conductivity, or magnetic permeability. Detailed descriptions of these "balloon" probes are provided in U.S. patent application Ser. No. 10/348,339, filed Jan. 21, 2003, the entire teachings of which are incorporated herein by reference.

Figure 1:
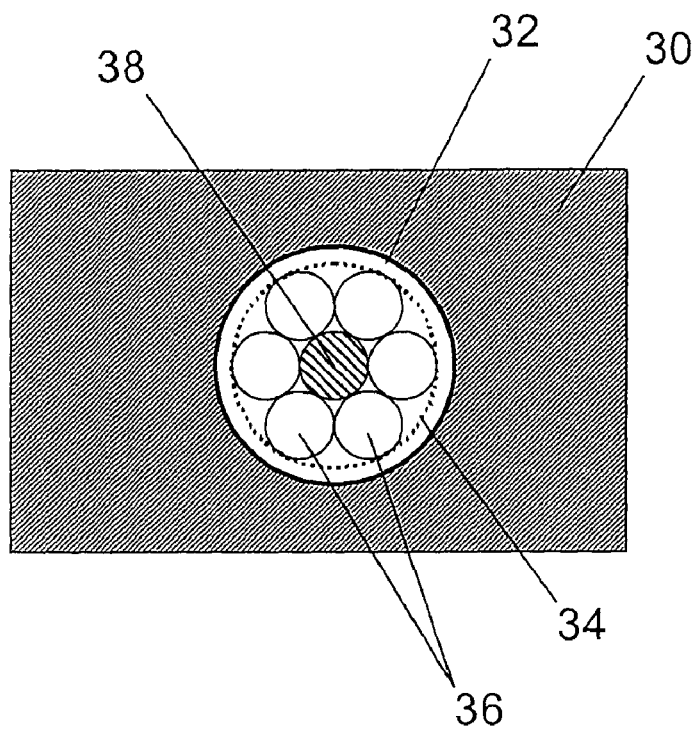
FIG. 1 is an illustration of a bolt hole probe with a fluid shuttle in accordance with the invention.

FIG. 1 shows a shuttle device for inspecting the inside of a circular opening 32 in a material under test (MUT) 30, such as a bolt hole. A flexible sensor or sensor array 34 is located between the central core 38 of the shuttle and the inner surface of the MUT. The core 38 may be an elastic material that can expand under pressure, such as a balloon that is inflated either pneumatically of hydraulically, so that the sensor 34 is near to or in contact with the MUT surface. In an embodiment, the flexible sensors or sensor arrays are eddy current sensors, described for example in U.S. Pat. No. 5,453,689 by Goldfine and Melcher, U.S. Pat. No. 5,047,719 by Johnson and Krampfner, and U.S. Provisional Application No. 60/276,997, the entire teachings of which are incorporated herein by reference. In addition a compliant solid (e.g., foam layer) may be included either between the solid shuttle and the array or between the array and the material under test.

In another embodiment, the core 38 of the shuttle is solid and surrounded by balloons 36. The sensor 34 is positioned between the balloons 36 and the MUT surface so that inflation of the balloons can move the sensor to be in contact with the test material. This use of multiple balloons can enhance the conformability of the sensor to the test surface as the pressure in individual balloons can be adjusted independently.

Figure 2:
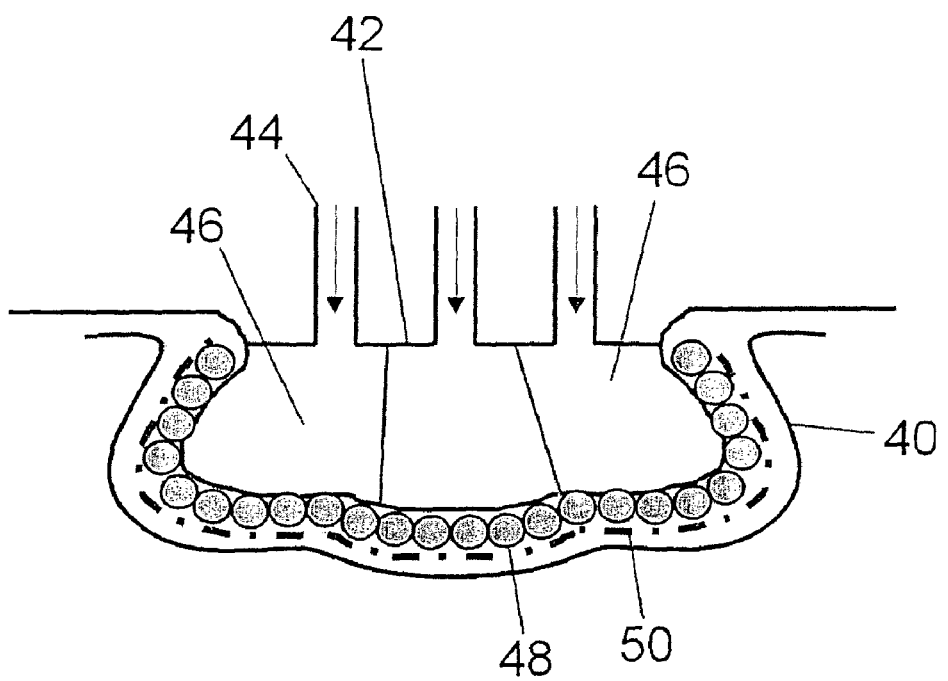
FIG. 2 is an illustration of a multiple fluid filled support chamber for a sensor array in accordance with the invention.

FIG. 2 shows a more complex design for a fluid filled support chamber. The sensor or sensor array 50 is positioned between the MUT surface 40 and one or more fluid filled support chambers or balloons 46. Fluid flow through conduits 44 in a back plate 42, preferably rigid, provides the pressure for inflating or deflating the chambers. Additional support or conformability can be provided by including rigid cylinder supports or support balloons 48 between the sensor 50 and the chambers 46. These balloons may be attached to each other and, in one embodiment, they may be enclosed in a larger balloon and attached to the inside of that balloon. In one embodiment, the composite balloon may be extruded as an integrated part with chambers representing the balloons. These chambers may or may not be cylindrical and may be of varying shapes. By introducing fluids into individual balloons or groups of balloons at a controlled pressure the balloons will expand to form individual cylinders. These micro-cylinders combine to form a macro-shape that follows the contour of the material under test surface. The kinematics of filling balloons to form to a complex shape can be computed with computer models so that the required amount of fluid within each balloon can be predetermined to form a specific shape. Also, non-cylindrical balloons might be used as part of the composite, and an outside membrane may also be introduced to provide a smooth continuous surface for mounting the sensor array and pressing against the material under test. In another embodiment, hard solid strips or cylinders of substrate material are pressed against the array by a fluid filled inner cushion that conforms to the shape of the material under test. This reverses the role of the hard shuttle with the foam outer layer. When cylinders are used a thread weave can be used to hold the composite together permitting the cylinder layer to conform to the shape of the slot while individual anchor cylinders are attached locally to the sensor array.

A variety of fluids can be used to expand the balloon element or chamber. These could include gases, such as air or nitrogen, or liquids, such as water, Theological fluids or ferrofluids. An advantage of electrorheological fluids and ferrofluids is that electrode elements can be added to the probe structure to impose electric or magnetic fields which, when passing through the electrorheological or ferro-fluids, causes a dramatic increase in the fluid viscosity and substantially cause the fluid to maintain it's shape. In this manner, the shape of the balloon structure can be "locked-in" after being expanded.

Figure 3:
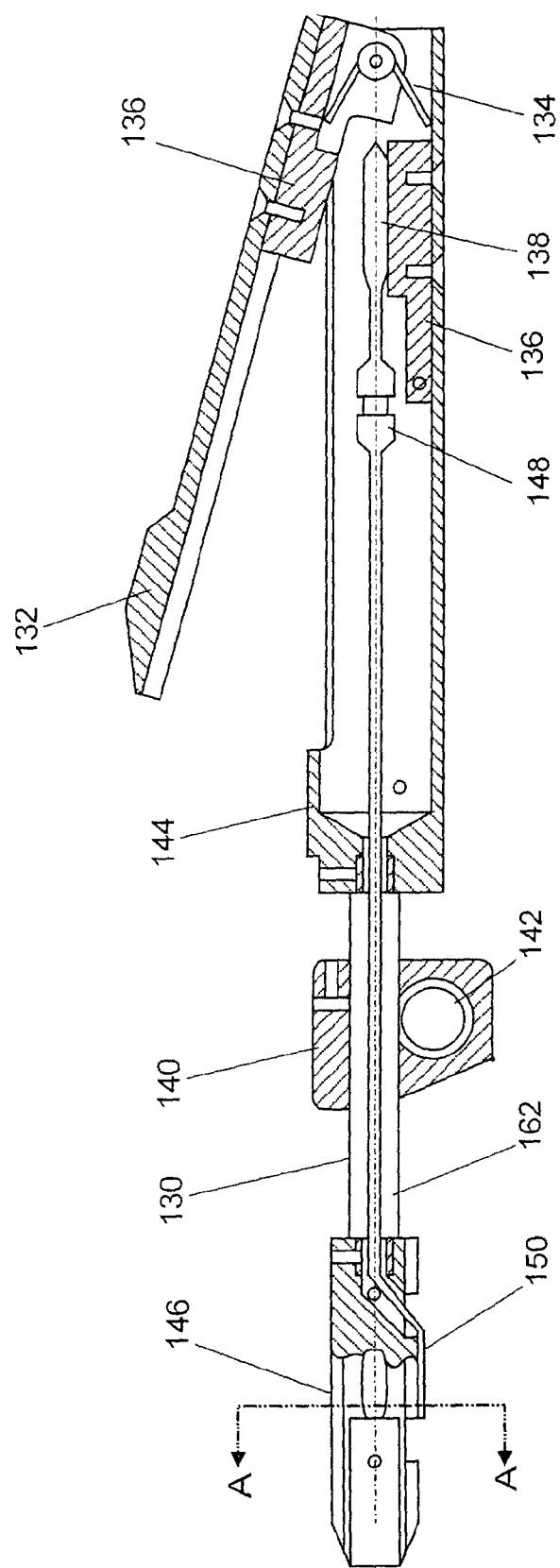
FIG. 3 is an illustration of a self-contained probe including both a shuttle and pressure source.
Figure 4:
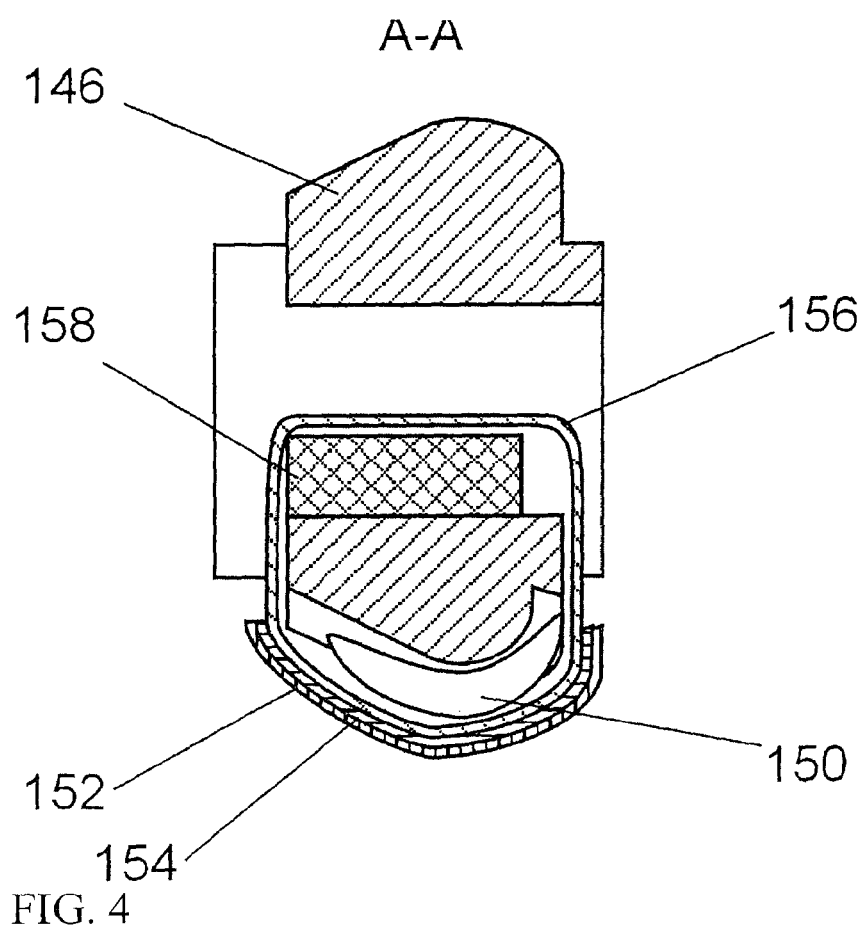
FIG. 4 is a cross-sectional view of the probe of FIG. 3.

An embodiment of an adjustable and conforming probe for inspection of curved surfaces such as engine disk slots is illustrated in FIG. 3 and FIG. 4. This probe includes a shuttle 146, a body 144, and a connection tube 130. The shuttle 146 holds a balloon 150 and a sensor or sensor array, and provides smooth motion of the sensor or sensor array across the surface of the test material during the inspection. The body 144 contains means for applying pressure to the balloon 150 in the shuttle. The connection tube 130, keeps the assembly together, provides a support for the position encoder 140, and provides a hydraulic connection 162 to the shuttle balloon. Expansion of the balloon 150 presses the sensor 154 against the material surface. The body 144 includes a second balloon 138 and adapters and connectors 148 that connect and seal to the open ends of both balloons 138 and 150. The body also contains a handle 132, which can create pressure in balloon 138 as it is sandwiched between a pair of balloon supports 136. A torsion spring 134 provides a force for returning the handle to the initial open position when the handle is released. The position encoder incorporates an encoder roller 142 that rotates as the axial position of the probe tube 130 changes with insertion into the test article. The encoder roller 142 is surrounded by flexible silicon tubing to ensure that there is sufficient friction for the encoder roller to rotate as the probe tube position changes.

An expanded view of the shuttle is illustrated in FIG. 4. A flexible eddy current sensor or sensor array 154 is attached to a flexible ring 156 that surrounds the balloon 150, part of the solid portion of the shuttle 146, and a foam spring 158. The balloon 150 presses the sensor 154 against the test material with a uniform force during the inspection. The flexible ring 156 transmits the motion from the foam spring 158 to the sensor 154, which allows the foam spring to return the sensor 154 to its initial position and deflate the balloon 150 upon completion of an inspection. An outer protective layer 152 is also used to protect the sensor 154 and balloon 150 from wear and shearing forces. Preferably, the flexible material for the sensor, the surrounding ring, and the outer protective wear material is Kapton™.

For inspections, the probe structure should be smaller that the slot in which the probe is to be inserted. In operation, the shuttle is slid into the test article with the balloon 150 deflated. Once inside the test article, the handle 132 is closed which compresses balloon 138 and inflates balloon 150. This, in turn, presses the sensor 154 against the surface of the test material for the inspection. After completion of the inspection, releasing the handle 132 causes the handle to move to the open position and the foam spring 158 inside the shuttle 146 deflates the balloon 150 back to its original form. Any fluid (gas or liquid) can be used to inflate and deflate the balloon. Typically, air or water is used.

Figure 5:
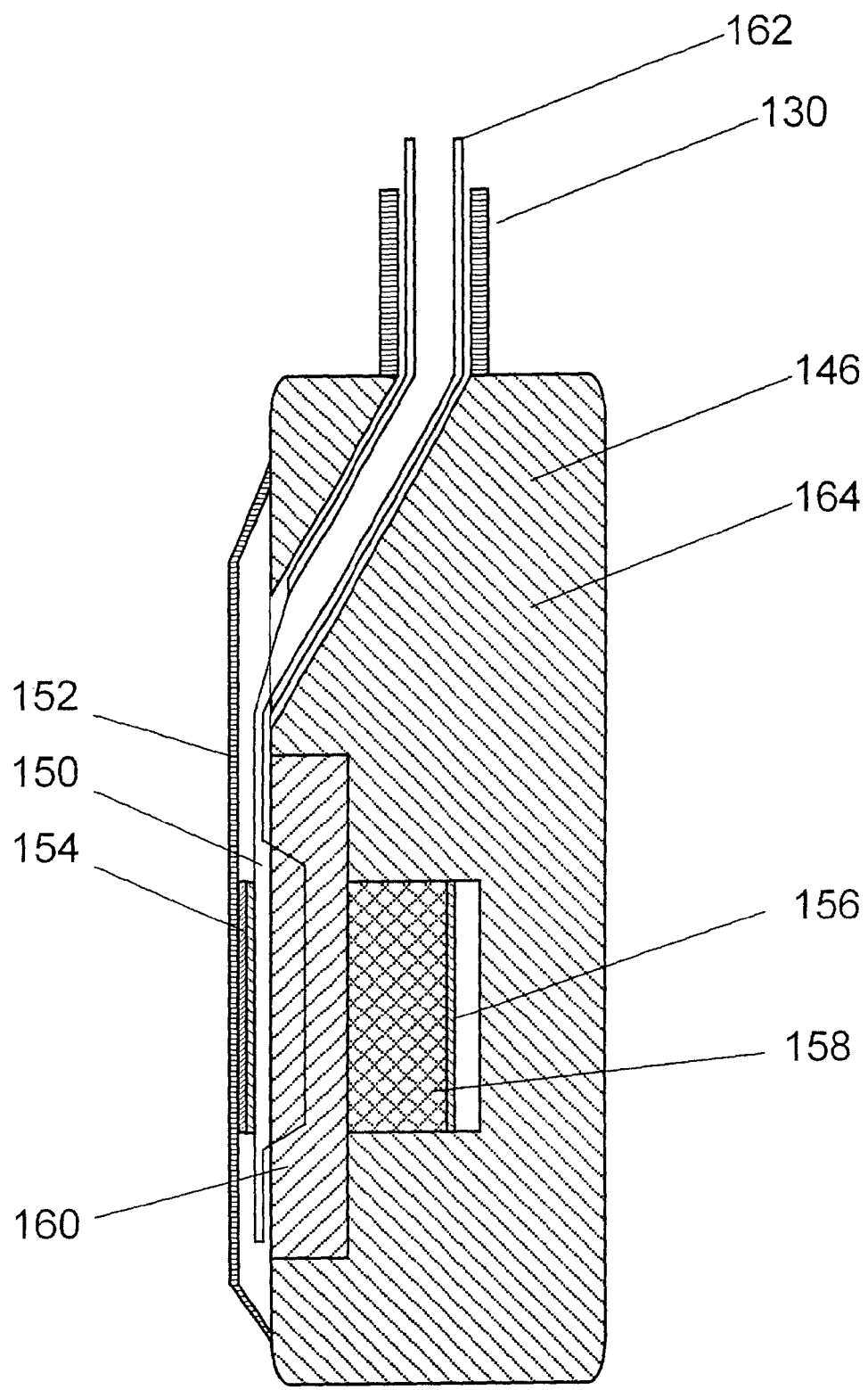
FIG. 5 is a cross-sectional view of a probe having a removable insert for ease of repair.
Figure 6:
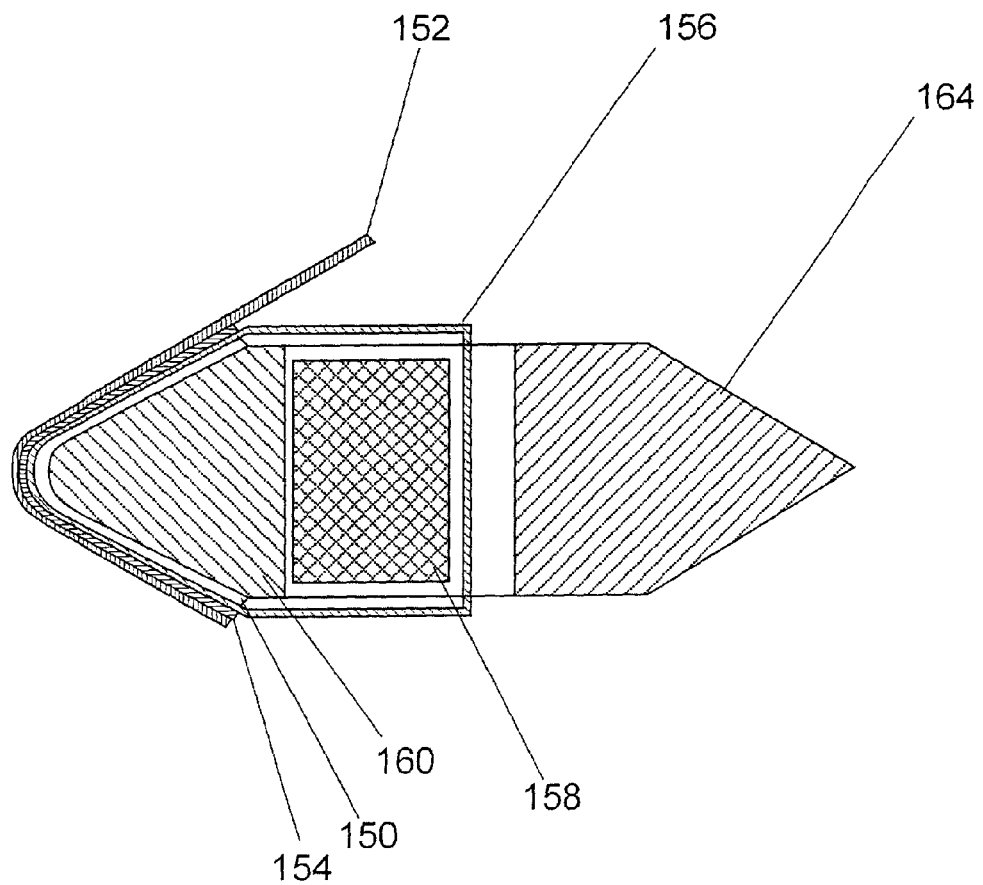
FIG. 6 is an expanded view of the probe of FIG. 5.

FIG. 5 and FIG. 6 show an alternative embodiment for the structure of the shuttle portion of the probe. In these embodiments, the shuttle 146 is split into two parts, a body 164 and a removable insert 160, with the removable insert attached to the body by means of a temporary adhesive. This modular design has the advantage that it allows rapid replacement of broken components. Removing the protection flexible layer 152 and the removable insert 160, provides easy access to the internal components of the shuttle.

Figure 7:
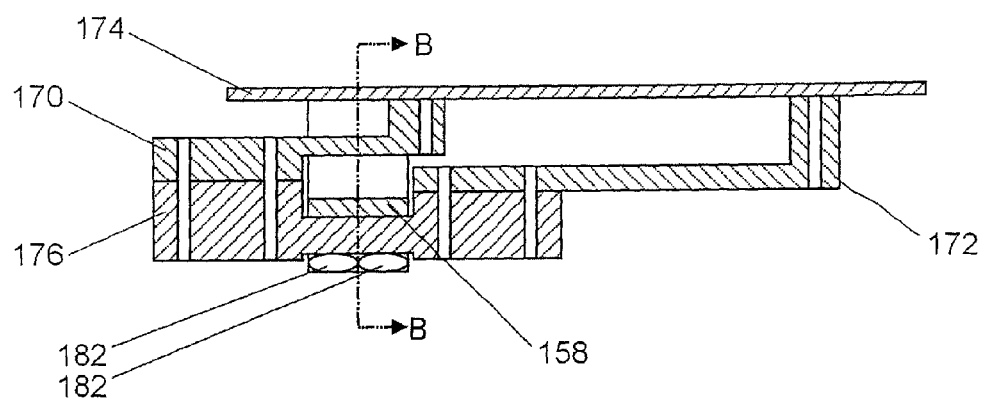
FIG. 7 is a cross-section view of a probe for a flexible eddy current sensor array.
Figure 8:
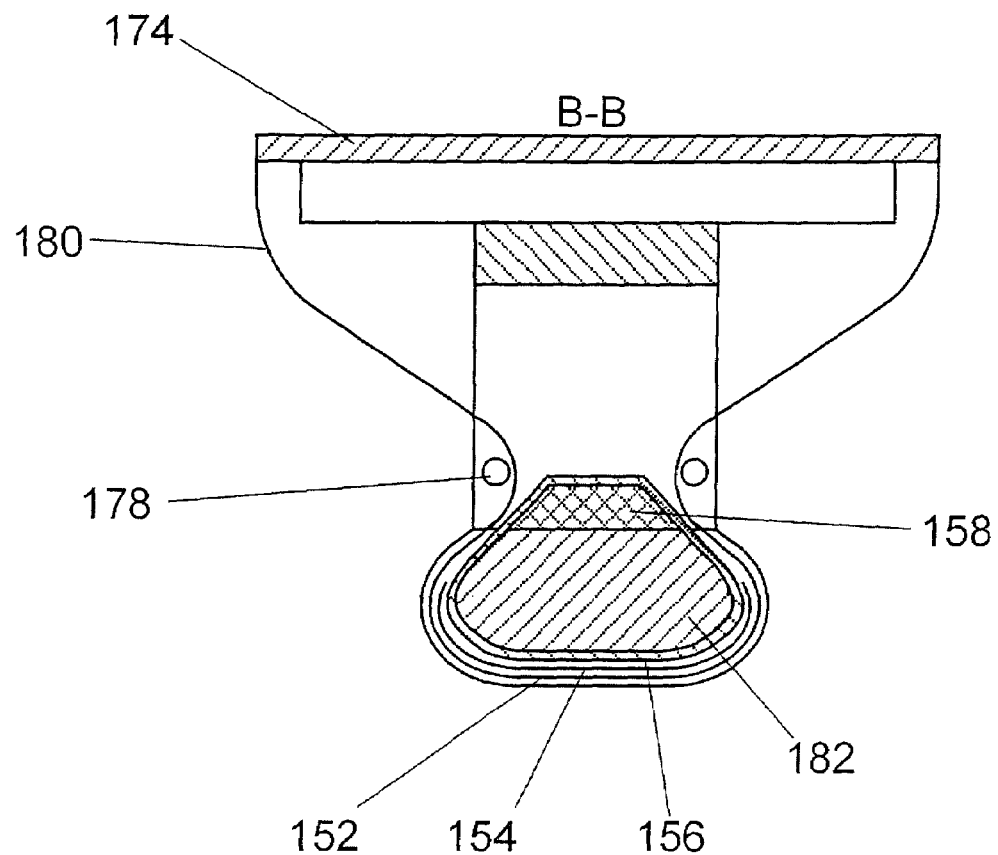
FIG. 8 is an expanded view of the probe of FIG. 7.
Figure 9:
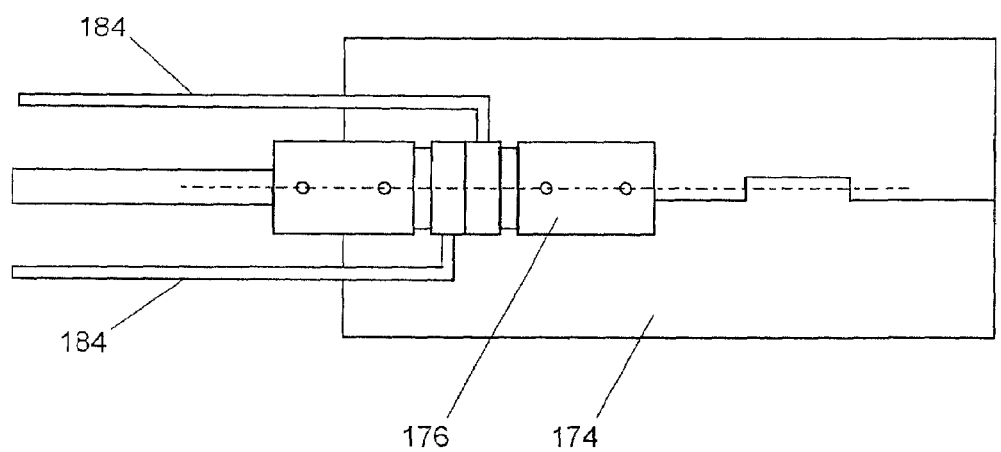
FIG. 9 is a bottom view of the probe of FIG. 7.

FIGS. 7–9 show an embodiment for a shuttle designed to accommodate a flexible eddy current sensor array having numerous leads for electrical connections to each of the sensing elements. The relatively large back plate 174 for the sensor provides a support structure for the bond pad connections to the sensing element leads. Support brackets 170 and 172 connect the back plate 174 to a mandrel 176. The mandrel carries balloons 182, a sensor array 154, foam spring 158, a flexible ring 156, and a protective flexible layer 152. The utility of each of these components is the same as was described for FIG. 4. The embodiment of FIG. 4 also includes a ring 178 that holds together flexible support structure 180 for the connection leads to the sensor array. Two or more balloons 182 are also oriented across the mandrel 176 for pressing the sensor against the material surface, such as an engine disk slot. The use of multiple balloons helps to force the sensor to conform to the surface of the test material even at edges, where the sensor may be entering or leaving the test article. This permits inspections close to the edges of engine disk slots and allows the sensor to conform to the surface geometry such as the chamfers at the ends of the slots. The sleeves 184 provide connections between the balloons 182 and the source of pressure.

Figure 10:
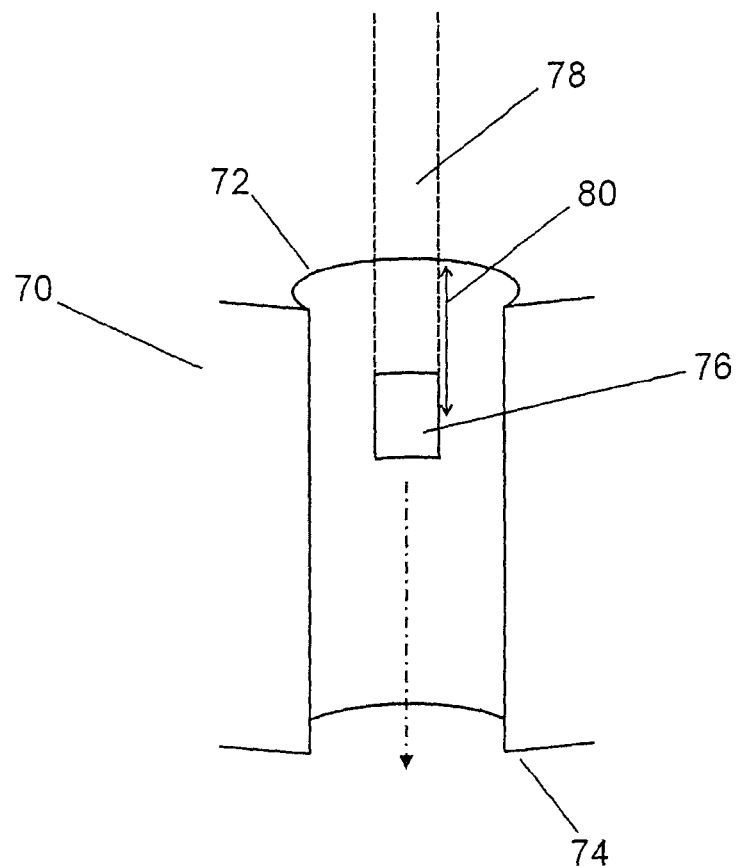
FIG. 10 is an illustration of a sensor probe and scan as the probe is inserted into a channel.
Figure 11:
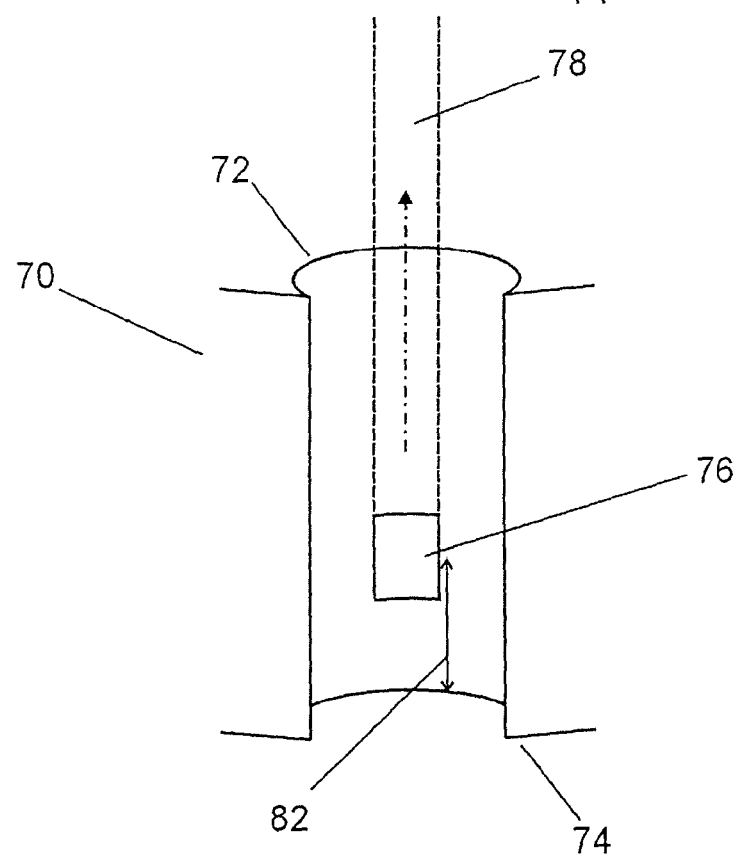
FIG. 11 is an illustration of a sensor probe and scan as the probe is withdrawn from a channel.
Figure 12:
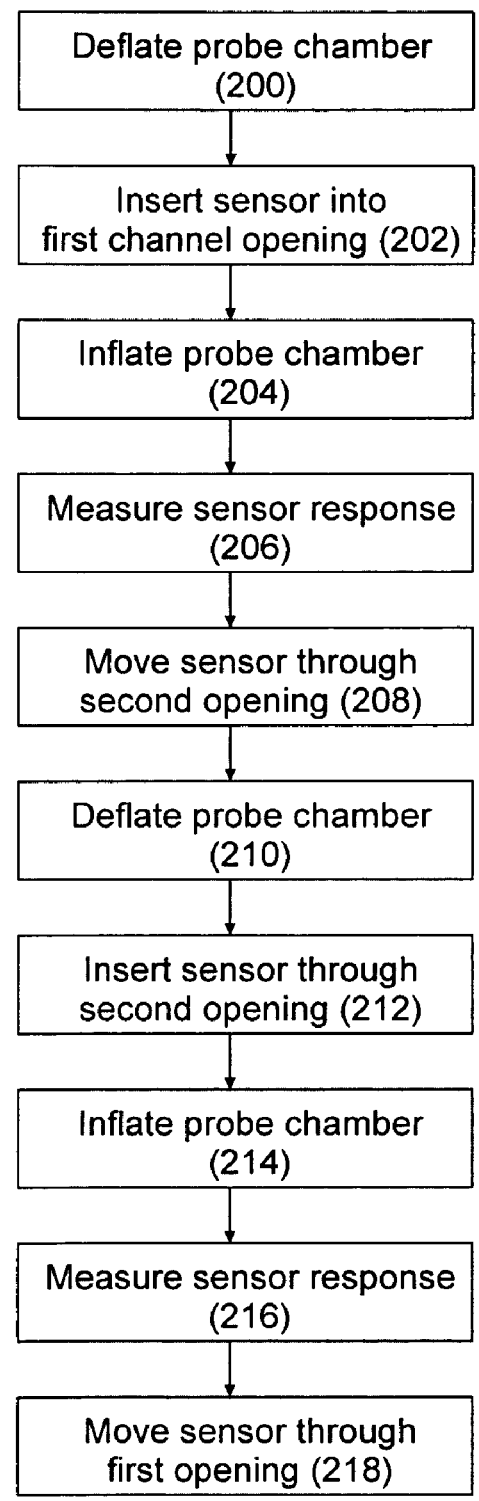
FIG. 12 is illustration of a sensor probe and scan as the probe is inserted into and withdraw from a channel.

In many applications the entire surface of the MUT must be inspected. For complete coverage, this requires that the sensor or sensor array be scanned over the entire surface, including the edges. As described herein, this is readily accomplished by taking measurements with the sensor or sensor array as it is comes out of the area of limited access or channel, such as an engine disk slot, bolt hole, or a narrow gap between surfaces. A procedure for performing this type of inspection is illustrated in FIGS. 10, 11, and 12. As shown in FIG. 10, an MUT 70 having a channel or region of limited access is inspected with a sensor or sensor array 76 attached to a balloon probe 78. A typical balloon probe and sensor assembly was shown in FIG. 3. With the balloon deflated 200, the sensor array 76 is placed a distance 80 from one side of the channel 72, 202. The balloon is then inflated 204 so that the sensor array is proximate to the MUT surface. A measurement scan is then taken 206 as the array is moved through an opening on the opposite side of the channel 74, 208. In one embodiment of the invention, the sensor assembly may be moved out of the second opening not all the way, such that the balloon probe 78 remains fully or partially inside the channel. After the sensor array has passed through the channel the balloon is deflated 210 and placed in the channel 212 a distance 82 away from the opposite end of the channel 74 as shown in FIG. 11. The balloon is then reinflated 214 so that the sensor array is again proximate to the test material. Another measurement scan is then performed 216 as the array is withdrawn from the channel 218.

Each measurement scan allows the properties along the channel in the scan direction to be measured. When the sensor 76 is an array, the result can be displayed as an image of the measurement response itself, in terms of the material properties or lift-off, or in terms of effective parameters obtained from filtering the response. A convenient method for converting the sensor response into these material or geometric properties is to use measurement grid methods as described in more detail in U.S. Pat. No. 5,453,689, the entire teachings of which are incorporated herein by reference. If the span of the sensor or sensor array does not cover the width of the channel, the sensor 76 can be scanned incrementally around the channel to ensure complete coverage.

To ensure complete coverage of the channel, the distances 80 and 82 are typically less than one-half of the length of the channel. This permits some overlap of the measurements over the central region of the channel. Preferably, the sensors are inserted approximately one-third of the distance into the channel. The individual scans of the measurement response can be displayed as separate images or plots. Alternatively, the overlap areas can be combined, as in an average of the responses, so that a single image or plot is obtained. As another alternative, one or more scan passes can be performed. The resulting image can then express some combination or comparison of the responses for the scans.

The inspections can be performed with any conformable sensor or sensor array that uses inflatable or deflatable bladders or balloons. Preferably, flexible eddy current sensor arrays are used, which are described in more detail in U.S patent application Ser. No. 10/102,620, filed Mar. 19, 2002, and Ser. No. 10/155,887, filed May 23, 2002, the entire teachings of both of which are incorporated herein by reference.

This method of deflating the balloon prior to insertion also extends the useful life of the sensor. Often, the insertion of a probe having a compressible or foam backing into an opening can introduce unintended mechanical stress on the flexible sensor, eventually leading to mechanical failure of the sensor, such as a broken conductor or wire. By inserting a deflated balloon and sensor into the channel, the mechanical stresses on the sensor associated with the sensor entering the channel are eliminated. By inflating the balloon with the sensor inside the channel, the mechanical stress on the sensor as it is withdrawn from the channel is more gradual and less likely to lead to sensor fatigue and failure.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method for inspecting a channel using a flexible sensor connected to at least one elastic member containing a pressurizable chamber for maintaining the sensor position proximate to a component surface, said method comprising:
   a first scan comprising inserting the sensor with a deflated chamber into a first end opening of the channel, inflating the chamber, and measuring the sensor response as the sensor is moved along the channel and through a second end opening of the channel;
   a second scan comprising inserting the sensor with a deflated chamber into the second end opening of the channel, inflating the chamber, and measuring the sensor response as the sensor is moved along the channel in the opposite direction as the first scan and through the first end opening of the channel; and
   combining measurement responses from first and second scans in opposite directions.

2. The method as claimed in claim 1 wherein the sensor is an eddy current sensor.

3. The method as claimed in claim 1 wherein the sensor is an eddy current sensor array.

4. The method as claimed in claim 1 wherein the sensor is inserted into the channel openings and inflated at a distance less than one-half the channel length.

5. The method as claimed in claim 4 wherein said distance is approximately one-third of the channel length.

6. The method as claimed in claim 1 wherein the combination is an average of the scans.

7. A method for inspecting a channel using a flexible sensor connected to at least one elastic member containing a pressurizable chamber for maintaining the sensor position proximate to a component surface, said method comprising:
   inserting the sensor with a deflated chamber into a first channel opening;
   inflating the chamber;
   measuring the sensor response as the sensor is moved along the channel to form a first scan;
   measuring the sensor response as the sensor is moved along the channel in the opposite direction to form a second scan; and
   combining measurement responses from first and second scans in opposite directions.

8. The method as claimed in claim 7 further comprising measuring sensor position.

9. The method as claimed in claim 7 wherein the sensor is an eddy current sensor.

10. The method as claimed in claim 9 wherein the channel is an engine disk slot and measuring the sensor response involves detecting the presence of crack.

11. The method as claimed in claim 9 wherein the channel is a bolt hole.

12. The method as claimed in claim 7 wherein the sensor is an eddy current sensor array.

13. The method as claimed in claim 7 wherein the sensor is inserted into the channel openings at a distance approximately one-third of the channel length.

14. The method as claimed in claim 7 wherein the combination is an average of the scans.

* * * * *